United States Patent [19]

Blakely et al.

[11] Patent Number: 5,024,840
[45] Date of Patent: Jun. 18, 1991

[54] ANTIMICROBIAL CARPET AND CARPET TILE

[75] Inventors: Lawrence W. Blakely; Michael A. Howe, both of LaGrange; Daniel F. Pinholster, Jr., Cartersville; Claude E. Terry, Kennesaw, all of Ga.; Robert H. McIntosh, Sr., Greensboro, N.C.

[73] Assignee: Interface, Inc., Atlanta, Ga.

[21] Appl. No.: 352,060

[22] Filed: May 15, 1989

Related U.S. Application Data

[63] Continuation-in-part of Ser. No. 190,370, May 5, 1988, Pat. No. 4,908,209, which is a continuation-in-part of Ser. No. 47,561, Apr. 27, 1987, Pat. No. 4,935,232, which is a continuation-in-part of Ser. No. 781,710, Oct 2, 1985, abandoned, Ser. No. 635,728, Oct. 9, 1984, abandoned, Ser. No. 713,445, Mar. 19, 1985, abandoned, Ser. No. 736,652, Apr. 21, 1985, Pat. No. 4,647,601, Ser. No. 744,730, Jun. 13, 1985, abandoned, each is a continuation-in-part of Ser. No. 570,952, Mar. 8, 1984, Pat. No. 4,608,289, which is a continuation of Ser. No. 523,734, Aug. 16, 1983, abandoned, which is a continuation of Ser. No. 226,006, Jan. 19, 1981, abandoned, which is a continuation of Ser. No. 930,879, Aug. 4, 1978, abandoned, which is a continuation-in-part of Ser. No. 224,057, Jul. 25, 1988.

[51] Int. Cl.$^5$ .............................. A01N 25/34
[52] U.S. Cl. ............................ 424/404; 424/78; 424/81; 424/82; 424/405; 424/83; 424/400; 424/402; 424/409; 424/443
[58] Field of Search ............ 424/404, 78, 81, 82, 424/83, 400, 402, 405, 409, 443

[56] References Cited

U.S. PATENT DOCUMENTS

| | | | |
|---|---|---|---|
| 2,202,124 | 4/1940 | Tattersal | 106/18.17 |
| 2,272,668 | 2/1942 | Honel | 558/113 |
| 2,337,424 | 12/1943 | Stoner et al. | 260/86 |
| 2,541,088 | 2/1951 | Nikawitz | 260/584 |
| 2,552,325 | 5/1951 | Kosolapoff | 260/461 |
| 2,592,564 | 4/1952 | Hardman | 106/273 |
| 2,676,122 | 4/1954 | McCarthy | 117/139.5 |
| 2,756,175 | 7/1956 | Goldstein et al. | 167/33 |
| 2,831,782 | 4/1958 | Zvanut | 117/127 |
| 2,872,351 | 2/1959 | Wedell | 117/121 |
| 2,891,878 | 6/1959 | Chamberlain | 428/421 |
| 2,922,738 | 1/1960 | McDermott et al. | 167/22 |
| 2,935,490 | 5/1960 | Havens et al. | 260/45.7 |
| 2,960,529 | 11/1960 | McCall et al. | 260/461 |
| 2,970,081 | 1/1961 | McCall et al. | 167/30 |
| 2,976,186 | 3/1961 | Thompson et al. | 260/45.8 |
| 2,997,454 | 8/1961 | Leistner et al. | 260/45.8 |
| 3,247,134 | 4/1966 | Hwa et al. | 260/2.2 |
| 3,279,986 | 10/1966 | Hyman | 167/42 |
| 3,280,131 | 10/1966 | Wakeman et al. | 260/286 |
| 3,294,775 | 12/1966 | Wasserman | 260/100 |
| 3,306,955 | 2/1967 | Lowes, Jr. | 424/404 X |
| 3,308,488 | 3/1967 | Schoonman | 252/106 |
| 3,312,623 | 4/1967 | Fitch et al. | 252/106 |
| 3,364,192 | 1/1968 | Leach | 260/94.9 |
| 3,404,140 | 10/1968 | Fukumoto et al. | 260/93.7 |
| 3,428,713 | 2/1969 | Bartlett et al. | 260/924 |
| 3,475,204 | 10/1969 | Patterson | 117/178.7 |
| 3,498,969 | 3/1970 | Lewis | 260/211 |
| 3,527,726 | 9/1970 | Gower et al. | 260/29.6 |
| 3,577,515 | 5/1971 | Vandegaer | 424/32 |
| 3,620,453 | 11/1971 | Gancberg et al. | 239/60 |
| 3,639,594 | 2/1972 | Notarianni et al. | 424/224 |
| 3,641,226 | 2/1972 | Partridge et al. | 260/990 |
| 3,671,304 | 6/1972 | Mischutin | 117/138 |
| 3,705,235 | 12/1972 | McIntosh et al. | 424/83 |
| 3,708,573 | 1/1973 | Yoshinaga et al. | 260/29.6 |
| 3,714,256 | 1/1973 | Samour et al. | 260/29.6 |
| 3,758,283 | 9/1973 | Matt | 44/62 |
| 3,762,415 | 10/1973 | Morrison | 128/290 |
| 3,769,377 | 10/1973 | De Selms | 260/958 |
| 3,776,806 | 12/1973 | Mayer et al. | 161/88 |
| 3,819,656 | 6/1974 | Barie, Jr. et al. | 260/343.7 |
| 3,857,934 | 12/1974 | Bernstein et al. | 424/404 X |

List continue on next page.

Primary Examiner—Thurman Page
Assistant Examiner—Robert H. Harrison
Attorney, Agent, or Firm—Kilpatrick & Cody

[57] ABSTRACT

A carpet and carpet tile resistant to the growth of Gram negative, Gram positive and fungal organisms which contains a polymeric non-plasticized PVC tuftlock precoat, fusion bonding adhesive, or secondary backing which has incorporated in it a phosphoric acid ester or its salt of the general formula:

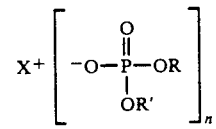

wherein R and R' are alkyl, oxyalkyl, polyoxyalkyl, aryl, aralkyl or alkaryl groups of $C_1$ to $C_{24}$, and one of R or R' can be H; X is a Group I metal ion, Group II metal ion, transition metal ion, or $NY_1Y_2Y_3Y_4$, where $Y_{1-4}$ are hydrogen, a hydrocarbon of $C_1$ to $C_{24}$, or a hydroxyalkyl group of $C_1$ to $C_{24}$; and there is at least one free hydroxyl group; and when X is $NY_1Y_2Y_3Y_4$ or a Group I metal ion, n is 1, when X is a Group II metal ion, n is 2; and when X is a transition metal, n is equal to the valence of the metal.

22 Claims, No Drawings

FOREIGN PATENT DOCUMENTS

| | | |
|---|---|---|
| 1162356 | 2/1984 | Canada . |
| 0035375 | 9/1981 | European Pat. Off. . |
| 2530584 | 1/1977 | Fed. Rep. of Germany . |
| 3014765 | 10/1981 | Fed. Rep. of Germany . |
| 3039437 | 5/1982 | Fed. Rep. of Germany . |
| 3248708.8 | 12/1982 | Fed. Rep. of Germany . |
| 1228031 | 11/1986 | Fed. Rep. of Germany . |
| 617854 | 6/1980 | Switzerland . |
| 1122664 | 11/1984 | U.S.S.R. . |
| 1036578 | 7/1966 | United Kingdom . |
| 1302894 | 1/1973 | United Kingdom . |
| 2042574 | 9/1983 | United Kingdom . |
| 2131029 | 1/1986 | United Kingdom . |

U.S. PATENT DOCUMENTS

| | | | |
|---|---|---|---|
| 3,873,648 | 3/1975 | Balde | 260/990 |
| 3,885,000 | 5/1975 | Beriger et al. | 260/956 |
| 3,896,101 | 7/1975 | McIntosh et al. | 260/93.7 |
| 3,897,491 | 7/1975 | Toy et al. | 260/543 P |
| 3,897,521 | 7/1975 | Beriger et al. | 260/948 |
| 3,919,410 | 11/1975 | McIntosh et al. | 424/78 |
| 3,920,836 | 11/1975 | McIntosh et al. | 424/315 |
| 3,925,442 | 12/1975 | Samour | 424/315 |
| 3,928,563 | 12/1975 | McIntosh et al. | 424/78 |
| 3,932,612 | 1/1976 | Burkhardt et al. | 424/78 |
| 3,933,947 | 1/1976 | Kishino et al. | 260/949 |
| 3,959,556 | 5/1976 | Morrison | 428/364 |
| 3,972,243 | 8/1976 | Driscoll et al. | 424/200 |
| 3,979,307 | 9/1976 | Kolaian et al. | 252/8.75 |
| 3,991,187 | 11/1976 | Hogberg et al. | 424/199 |
| 4,004,001 | 1/1977 | Large et al. | 424/200 |
| 4,006,204 | 2/1977 | Rajadhyaksha et al. | 260/958 |
| 4,024,324 | 5/1977 | Sparks | 526/2 |
| 4,025,583 | 5/1977 | Mead et al. | 260/925 |
| 4,039,636 | 8/1977 | Claus et al. | 260/963 |
| 4,071,552 | 1/1978 | Ferland et al. | 260/562 R |
| 4,083,860 | 4/1978 | Ruf | 260/403 |
| 4,094,970 | 6/1978 | Behrenz et al. | 424/78 |
| 4,107,292 | 8/1978 | Nemeth | 424/78 |
| 4,110,504 | 8/1978 | Hull et al. | 424/97 |
| 4,119,724 | 10/1978 | Thizy et al. | 424/45 |
| 4,139,616 | 2/1979 | Ducret et al. | 424/222 |
| 4,152,421 | 5/1979 | Tsutsumi et al. | 424/57 |
| 4,165,369 | 8/1979 | Watanabe et al. | 424/70 |
| 4,235,733 | 11/1980 | Watanabe et al. | 424/70 |
| 4,259,078 | 3/1981 | Kleber et al. | 8/188 |
| 4,272,395 | 6/1981 | Wright | 252/106 |
| 4,276,418 | 6/1981 | Howarth | 544/243 |
| 4,289,634 | 9/1981 | Lewis et al. | 252/37.5 |
| 4,343,853 | 8/1982 | Morrison | 428/233 |
| 4,361,611 | 11/1982 | Schafer et al. | 428/96 |
| 4,363,663 | 12/1982 | Hill | 106/18.31 |
| 4,401,712 | 8/1983 | Morrison | 428/289 |
| 4,432,833 | 2/1984 | Breese | 162/138 |
| 4,442,095 | 4/1984 | Johnston | 544/120 |
| 4,442,096 | 4/1984 | Johnston | 424/250 |
| 4,560,599 | 12/1985 | Regen | 428/36 |
| 4,935,232 | 6/1990 | McIntosh | 424/78 |

OTHER PUBLICATIONS

Keil, et al., *Chem. Abstracts* 76, 101944k (1972) Ger. Offen. 2,030,256.

Sudakova, et al., *Chem. Abstracts* 70, 56711v (1969) (U.S.S.R. 229,879).

Gialkdi, et al., *Chem. Abstracts* 43, 6363a (1949) (*Farm. sci. e tec.* 4, 166–175.

Tak Chemicals Ltd. 1580026 (Jun. 1977).

McCoy *Microbiology of Cooling Water* 94–95 (Chemical Pub. Co., N.Y. 1980).

Yuan, et al., *Phosphorus and Sulphur*, vol. 18, 323–326 (1983).

Nakamura, *Journal of Radioanalytical Chemistry*, 52 (2), 343–354 (1979).

Nakamura, *Journal of Radioanalytical Chemistry*, 44, 37–47 (1978).

Partridge, et al., *J. Inorg. Nucl. Chem.*, 31, 2587–2589 (1969).

Tachimori, et al., *Journal of Radioanalytical Chemistry*, 67 (2), 329–337 (1981).

Honaker, et al., *J. Inorg. Nucl. Chem.*, 39, 1703–1704 (1977).

J. Perka, et al., *Tenside Detergents*, 15, 295–298 (1978)6.

Sorbe, et al., *Quim. Apl. Jorn. Com. Esp. Deterg.*, 11th, 415–430 (1980).

Yoshihira Koda, et al., "The Synthesis of Surfactant and the Use Thereof", pp. 96–99 and 436–447 (1977).

Takehiko Fujimoto, "Introduction in New Surfactant", p. 295–297 (1974).

*J. Inorg. Nucl. Chem.*, 38, 2127–2129 (1976).

Matsui, et al., Chem. Abstracts 82, 141561 (1974) (JP 74 24,806).

Ogasawara, et al., *Chem. Abstracts 81, 107078f (1974)* (U.S. Pat. No. 3,799,904).

Hall, et al. *Chem. Abstracts* 80, 123000 (1973) *ASLE Trans.* 16(4), 291–296.

ANTIMICROBIAL CARPET AND CARPET TILE

This application is a continuation-in-part of:

(1) U.S. patent application Ser. No. 190,370, entitled "Biocidal Delivery System and Method of Preparation Thereof," filed May 5, 1988, now U.S. Pat. No. 4,908,209, by Robert H. McIntosh, Jr., Albin F. Turbak, and Robert H. McIntosh, Sr.; which is a continuation-in-part of U.S. Ser. No. 047,561, filed Apr. 27, 1987, now U.S. Pat. No. 4,935,232, entitled "Microbiocidal Composition and Method of Preparation Thereof" by Robert H. McIntosh; which is a continuation-in-part of the following applications: U.S. Ser. No. 781,710 filed Oct. 2, 1985, now abandoned; U.S. Ser. No. 635,728 filed Oct. 9, 1984, now abandoned; U.S. Ser. No. 713,445 filed Mar. 19, 1985, now abandoned; U.S. Ser. No. 736,652 filed May 21, 1985, now U.S. Pat. No. 4,647,601; U.S. Ser. No. 744,730 filed June 13, 1985, now abandoned; all of which are continuations-in-part of U.S. Ser. No. 570,952 filed Mar. 8, 1984 now U.S. Pat. No. 4,608,289, which is a continuation of U.S. Ser. No. 523,734 filed Aug. 16, 1983, now abandoned, which is a continuation of U.S. Ser. No. 226,006 filed Jan. 19, 1981, now abandoned, which is a continuation of U.S. Ser. No. 930,879 filed Aug. 4, 1978, now abandoned; and (2) U.S. patent application Ser. No. 224,057, entitled "Latex Fusion Bonded Pile Carpets and Carpet Tile," filed July 25, 1988 by Lawrence W. Blakely and Michael A. Howe.

BACKGROUND OF THE INVENTION

This invention is in the field of carpet manufacture, and in particular relates to carpet and carpet tile prepared with a biocidal tuftlock precoat or fusion bonding adhesive.

Bacteria, fungi, viruses, algae and other microorganisms are always present in our environment. Such microorganisms are frequently an essential part of ecological systems, industrial processes, and healthy human and animal bodily functions, such as digestion. In other instances, however, microorganisms are highly undesirable as a cause of illness, odors, and damage or destruction of a wide variety of materials.

The species and numbers of microorganisms present in the environment are dependent on the nutrients and the moisture available for growth, as well as on the humidity and temperature. Nutrients for microorganisms generally abound in the normal environment.

A particularly good environment for the growth of microorganisms is found in carpet and carpet tile. Bacteria and fungi are deposited on the carpet through the everyday traffic of people and animals, food and beverages spilled on the carpet, and animal and infant waste. Further, airborne microorganisms carried in from outside or carried through the heating or cooling system can accumulate on carpet. Soil and moisture in carpet provide nutrients for the growth of the microbes. Moreover, certain bacteria are capable of remaining viable in a dormant state on carpet for long periods of time until they are provided adequate sustenance.

Organic materials used in the construction of carpet and carpet tile can be a source of nutrition for certain microorganisms. Carpet fibers are typically made from polyamides, such as nylon and wool, or from polyester, which are biodegradable. Tuftlock precoat or fusion bonding adhesives typically contain organic polymers in combination with fillers and other additives. Microbial digestion of these organic materials can result in the deterioration as well as the discoloration of the carpet over time. Further, the unhealthy accumulation of bacterial or fungal growth can create a foul odor.

It has proved difficult, however, to develop a microbiocidal composition that is effective in controlling the growth of the wide variety of unwanted microorganisms and is, at the same time, safe for use around human beings and animals. Another difficulty is the extreme variability of response of various microorganisms to conventional microbiocidal agents. Even within bacteria, Gram-negative and Gram-positive bacteria respond differently to antibiotics. Further, antibiotics that are effective against procaryotic organisms are usually ineffective against eucaryotic microorganisms such as fungi and yeasts.

U.S. patent application Ser. No. 047,561 entitled "Microbiocidal Composition and Method of Preparation" filed Apr. 27, 1987, by Robert H. McIntosh disclosed a broad spectrum, safe, biocidal composition having the following general formula:

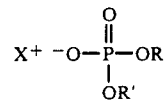

wherein R and R' are an alkyl, aryl, aralkyl or alkaryl group, one of R or R' can be H, X is a Group I metal ion, Group II metal ion, transition metal ion, or an organic ion such as an ammonium ion, and there is at least one free hydroxyl group. The biocide can be effectively incorporated into a large variety of substrates, such as detergents, coatings, plastics, wood and wood products.

U.S. Pat. No. 4,608,289 to McIntosh discloses a carpet which contains a dialkylalkoxyammonium dialkylphosphate in the backing coat of the carpet as a sanitizing agent against Gram Negative, Gram Positive and fungal organisms.

Antimicrobial agents now being marketed for use in carpet fibers include Dow Corning TM 5700 Antimicrobial Agent for textile fibers and OBPA (10,10-oxybisphenozarsine), marketed by Morton Thiokol, Inc. Dow Corning TM 5700 Antimicrobial Agent, marketed under the tradename SYLGARD, is a silicone quaternary amine of the general formula $[CH_3(CH_2)_{17}N(CH_3)_2 (CH_2)_3Si(OCH_3)_3]^+Cl^-$. It is applied to the carpet fiber and is activated in the presence of moisture. It does not kill microorganisms in the absence of moisture. Further, it is only active against Gram positive organisms. OBPA is highly toxic.

In addition to hygenic aspects of carpet construction, consideration must also be given to carpet durability and manufacturing versatility. The type of adhesive used for the tuftlock precoat or fusion bonding adhesive is important to these considerations.

The most widely used method of manufacture of fusion bonded carpet presently involves the use of a nonlatex PVC (polyvinyl chloride) plastisol formulation as the bonding adhesive. Typically, PVC plastisol is dispensed over a support layer to form an adhesive layer that penetrates into the support layer. The adhesive layer is then contacted with pile forming yarn. The PVC plastisol is cured, creating a product in which the yarn fibers are secured in the PVC layer and thereby bonded to the support layer. Increased strength may be obtained by bonding a secondary backing to the support layer.

Alternatively, pile yarn can be woven or tufted through a primary backing. The yarn is then adhered to the backing with a tuftlock precoat. This type of carpet, in which the yarn is mechanically as well as adhesively attached to the backing, is generally termed "woven" or "tufted" carpet. PVC plastisol formulations are commonly used as the polymeric base material in the tuftlock adhesive precoats.

In order to make a durable carpet in which the support layer does not peel away from the secondary backing, the adhesive which has permeated into the support layer must contact and bond with the material forming or adhering the secondary backing. The use of a non-latex plasticized PVC as the yarn locking adhesive limits the variety of backing structures that may be applied to the carpet. This is true because nonlatex PVC plastisol does not bond strongly to common carpet backing materials such as bitumen, EVA (ethylene-vinylacetate), APP (atactic polypropylene), hot melts, urethanes, and SBR (styrene-butadiene). Furthermore, PVC plastisol is relatively expensive.

A carpet and carpet tile is needed for industry and the home that is not only resistant to the attack and growth of microorganisms, but that can be made with a variety of secondary adhesives and backings compatible with its assorted uses.

It is therefore an object of the present invention to provide carpet and carpet tile which is resistant to the growth of Gram negative bacteria, Gram positive bacteria, and fungi.

It is a further object of the present invention to provide carpet and carpet tile which maintains its resistance to microbial growth after cleaning or processing.

It is another object of the present invention to provide carpet and carpet tile which is rendered resistant to microbial growth without substantially adding to the cost of the product.

It is a still further object of the present invention to provide a method to prepare antimicrobial carpet and carpet tile.

It is yet another object of the present invention to provide a carpet and carpet tile which has a yarn locking adhesive which is compatible with a wide variety of adhesives and secondary backings.

It is a further object of the present invention to provide a carpet which is durable and economical.

SUMMARY OF THE INVENTION

The present invention is carpet and carpet tile which is resistant to the attack and growth of Gram positive bacteria, Gram negative bacteria and fungal organisms. The carpet contains a tuftlock precoat or fusion bonding adhesive which has incorporated in it a phosphoric acid ester of the general formula:

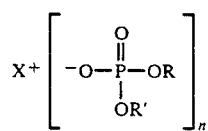

wherein R and R' are independently alkyl, oxyalkyl, polyoxyalkyl, aryl, aralkyl or alkaryl groups of $C_1$ to $C_{24}$, and one of R or R' can be H; X is a Group I metal ion, Group II metal ion, transition metal ion, or $NY_1Y_2Y_3Y_4$, where $Y_{1-4}$ are hydrogen, a hydrocarbon of $C_1$ to $C_{24}$, or a hydroxyalkyl group of $C_1$ to $C_{24}$; and there is at least one free hydroxyl group. When X is $NY_1Y_2Y_3Y_4$ or a Group I metal ion, n is 1. When X is a Group II metal ion, n is 2. When X is a transition metal, n is equal to the valence of the metal.

The tuftlock precoat or the fusion bonding adhesive includes a non-PVC plastisol polymer or copolymer. A preferred embodiment is carpet and carpet tile product with the phosphoric acid ester in a latex adhesive. An especially preferred embodiment is carpet prepared with a precoat or adhesive of the biocidal phosphoric acid derivative in a vinyl acetate-ethylene copolymer.

It has been discovered that the biocidal phosphoric acid ester diffuse from the primary adhesive to the upper end of the carpet fibers, providing protection from bacterial and fungal growth to the carpet base as well as throughout the fiber. The continuous migration of the phosphoric acid ester from the precoat or adhesive to the fiber imparts long term effective microbial protection to the carpet.

In another embodiment of the present invention, the phosphoric acid derivative is added to the secondary backing of the carpet to provide protection from microbial growth between the floor and the carpet.

DETAILED DESCRIPTION OF THE INVENTION

The present invention is carpet and carpet tile which is resistant to the growth of Gram negative bacteria, Gram positive bacteria, and fungal organisms over an extended period. The carpet represents a significant advancement over the prior art, in that it does not lose its antimicrobial effect when the carpet is cleaned or processed. The carpet or carpet tile includes a tuftlock precoat or a fusion bonding adhesive which contains a biocidal mono- or di-substituted phosphoric acid of the general formula:

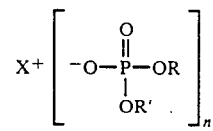

wherein R and R' are independently alkyl, oxyalkyl, polyoxyalkyl, aryl, aralkyl or alkaryl groups of $C_1$ to $C_{24}$, and one of R or R' can be H; X is a Group I metal ion, Group II metal ion, transition metal ion, or $NY_1Y_2Y_3Y_4$, where $Y_{1-4}$ are hydrogen, a hydrocarbon of $C_1$ to $C_{24}$, or a hydroxyalkyl group of $C_1$ to $C_{24}$; and there is at least one free hydroxyl group. When X is $NY_1Y_2Y_3Y_4$ or a Group I metal ion, n is 1. When X is a Group II metal ion, n is 2. When X is a transition metal, n is equal to the valence of the metal.

Examples of the alkyl, oxyalkyl, polyoxyalkyl, aralkyl and alkaryl R or R' groups include straight chain, branched chain or cyclic alkyl groups, polyoxyethylene having from 1 to 12 ethylene oxide units, polyoxypropylene having 1 to 8 propylene oxide units, phenyl, alkylphenyl, and alkoxyphenyl.

In a preferred embodiment, the biocidal phosphoric acid derivative is present as a trisubstituted ammonium salt. A preferred derivative is the di-(2-hydroxyethyl)-cocoamine salt of a monoalkylphosphoric acid. The phosphoric acid derivative can also be a metal salt which includes, for example, sodium or potassium (Group IA metals), magnesium (Group IIA metal), or zinc (transition metal). Selection of the positive ion does affect biocidal activity, principally the anti-Gram negative bactericidal activity, although the phosphoric acid moiety appears to be the primary source of biocidal activity.

The tuftlock precoat for tufted or woven carpet and the fusion bonding adhesive for fusion bonded carpet are collectively referred to below as "primary adhesives". The term carpet as used herein includes carpet and carpet tile.

PREPARATION OF THE BIOCIDAL PHOSPHORIC ACID ESTER

The biocidal phosphoric acid ester can be prepared by methods known to those skilled in the art. The majority of such methods provide a product mixture of mono- and di-substituted phosphoric acids which is hard to separate. It has been discovered that phosphoric acid esters with at least one free hydroxyl group are more biocidally active than phosphoric acid derivatives with n free hydroxyl groups. If a synthetic method is used which results in a mixture of mono- and di-substituted phosphoric acids, and the phosphoric acid mixture is reacted with a base to form a salt, the product mixture will contain a biocidally active salt of a monosubstituted phosphoric acid and a biocidally less active salt of a disubstituted phosphoric acid. For economy of time and expense in commercial manufacturing, this mixture of substituted phosphoric acid salts may be used without further purification in the preparation of the primary adhesive.

The following example describes one method for the preparation of phosphoric acid esters. This example, as well as all other examples provided herein, are illustrative only and are not intended to limit the scope of the invention.

EXAMPLE 1

Preparation of Biocidal Phosphoric Acid Ester

The phosphoric acid ester can be prepared by reacting 1 mole of phosphorus pentoxide with 3 moles of alcohol, such as 2-ethylhexanol, at a temperature of between about 60° C. and 120° C. Phosphorus pentoxide is slowly added to the alcohol while the mixture is agitated. Completion of the reaction is determined by titration of a sample of the resulting acid with a solution of potassium or sodium hydroxide. The reaction products include dialkyl phosphoric acid and monoalkyl phosphoric acid.

Microbiocidal activity is tested by plating a microorganism onto Trypticase Soy Nutrient Agar, or other appropriate media, punching 11 mm diameter, 5 mm deep holes into the agar, and applying 0.05 ml of each of the undiluted test compounds into the holes. The petri dish is examined for growth of the microorganism after incubation for 24 hours at 30° C. The diameter of the clear area surrounding the hole containing the compound being tested is indicative of the degree of antimicrobiocidal activity.

EXAMPLE 2

Preparation of Ammonium Salt of Phosphoric Acid Ester

A preferred method to form the ammonium salt of the phosphoric acid ester is by the neutralization of two moles of the reaction product of Example 1 with 1.3 moles of an amine such as bis(hydroxyethyl)cocoamine, by heating the mixture at a temperature of between 60° C. and 120° C. until the reaction is complete. Since disubstituted phosphoric acid is a stronger acid than monosubstituted phosphoric acid, the disubstituted phosphoric acid bonds preferentially with the amine, forming (assuming 50% monoalkyl and 50% dialkyl phosphoric acid in the Example 1 product mixture) approximately 1.0 mole of the ammonium salt of the disubstituted phosphoric acid, 0.3 mole of the ammonium salt of the monosubstituted phosphoric acid, and 0.7 mole of free monosubstituted phosphoric acid.

EXAMPLE 3

Preparation of Metal Salts of Phosphoric Acid Ester

Metal salts of phosphoric acid esters can be prepared by mixing a metal salt such as magnesium acetate or zinc acetate with the phosphoric acid ester, warming to dissolve, and then vacuum stripping off the acetic acid.

Specifically, salts of 2-ethylhexylphosphoric acid were prepared by mixing the acid with either magnesium (Group I metal), or zinc (transition metal), as follows.

| | |
|---|---|
| 1. Magnesium (acetate) 2.4 $H_2O$ | 20 gram |
| 2-Ethylhexyl phosphoric acid | 53 gram |
| 2. Zinc (acetate) 2.2 $H_2O$ | 15 gram |
| 2-Ethylhexyl phosphoric acid | 53 gram |

The metal salt was first mixed with the 2-ethylhexyl phosphoric acid, the solution warmed to dissolve the metal acetate, and then after dissolution, the acetic acid was stripped off. The resulting products were clear, colorless, viscous liquids. The magnesium and zinc salts of the phosphoric acid derivatives were washed, and then evaluated for biocidal activity using the following standard cup method test procedure.

A sterile nutrient agar solution was prepared. The nutrient agar was inoculated with a 24 hour culture of either *Staphylococcus aureus* (Gram positive) or *Pseudomonas aeruginosa* (Gram negative) organism. The inoculated agar was poured into 100×15 mm sterile petri dishes and allowed to solidify at room temperature. After solidification, small reservoirs were punched for the compounds to be tested. Magnesium 2-ethylhexylphosphoric acid was added to one well and zinc 2-ethylhexylphosphoric acid was added to another. The plates were then incubated 24 hours at 30° C. and examined for zones of inhibition.

The zone of inhibition of Staphylococcus was 15 mm for the magnesium 2-ethylhexylphosphoric acid and 19 mm for the zinc 2-ethylhexylphosphoric acid. No inhibition of the Pseudomonas was observed, however, the results clearly demonstrate that Group II and transition metal salts of the alkyl phosphoric acid have bactericidal activity.

PREPARATION OF BIOCIDAL TUFTLOCK PRECOAT OR FUSION BONDING ADHESIVE

The primary adhesive in the antimicrobial carpet of the present invention includes a polymer or copolymer other than a plasticized polyvinyl chloride which has suitable adhesive strength to bind the carpet fibers to the primary backing. A preferred embodiment is carpet and carpet tile product with a latex adhesive. Examples are polymers and copolymers of vinyl acetate-ethylene, styrene-butadiene, vinylidene chloride, vinyl chloride, cellulose acetate butyrate, vinyl chloride-acrylonitrile, vinyl acetate-acrylic acid, vinylidene chloride-acrylonitrile, acrylic acid-methacrylic acid, butadiene-acrylonitrile, acrylic acid-styrene, acrylonitrile-styrene, acrylonitrile-acrylic acid, acrylonitrile-alkyl acrylate, vinyl acetate acrylate ester, and acrylonitrile butadiene styrene.

A preferred embodiment is carpet prepared with a vinyl acetate-ethylene (VAE) copolymer. A VAE primary adhesive which contains a high vinyl acetate content, for example greater than 50% vinyl acetate, provides superior fiber lock performance and wear durability. U.S. Ser. No. 224,057, entitled "Latex Fusion Bonded Pile Carpets and Carpet Tile", filed July 25, 1988, by Lawrence W. Blakely and Michael A. Howe, and incorporated herein by reference, describes a fusion bonded carpet in which the pile yarn is secured in a latex adhesive base which includes a latex polymer such as vinyl acetate-ethylene.

The biocidal phosphoric acid ester can be mixed with the polymeric adhesive in a ratio of 0.2 to 10 parts by weight of the phosphoric acid ester or its salt to 100 parts by weight of polymeric solids. A preferred ratio is 2.5 to 3 parts by weight of the phosphoric acid ester to 100 parts by weight of polymeric solids. If more than 10 parts by weight of the phosphoric acid ester or its salt is used in latex compositions, the compound can act as a plasticizer, softening the adhesive, and decreasing carpet durability.

When the phosphoric acid ester or its salt is added to commercially prepared solutions of latex polymeric solids, a problem of precipitation or insolubility sometimes occurs. It is thought that the acidic phosphoric acid moiety may cause premature polymerization or coagulation of the latex. This problem is especially acute when the pH of the latex solution is greater than 7.0.

It has been discovered that this problem can be avoided by adding the phosphoric acid ester to the polymeric latex solution in an ammoniated form. For example, a solution of phosphoric acid ester or its salt, water and ammonia can be prepared which converts approximately all of the free hydroxyl groups in the phosphoric acid solution to the corresponding ammonium salts. This ammoniated solution is then added to the polymeric latex solution.

The following is an example of a method to prepare an ammoniated solution of the biocidal phosphoric acid ester or its salt which is compatible with many commercial latex preparations.

EXAMPLE 4

Preparation of Ammoniated Solution of Phosphoric Acid Ester

An ammoniated solution of the di-(2-hydroxyethyl)-cocoamine salt of 2-ethylhexylphosphoric acid is prepared by:
  i) mixing 9.24 parts by weight of water with 16.65 parts by weight of a 28-30% solution of ammonium hydroxide; and then
  ii) slowly adding the solution from step i) to 74.10 parts by weight of the product of Example 3, keeping the temperature at or below 120° F.

EXAMPLE 5

Preparation of Solution of Latex Polymer and Ammoniated Phosphoric Acid Ester

The product of Example 4 can be added to a polymeric solution of latex solids in a range of 0.3 to 13.50 parts by weight of solution in Example 4 (corresponding to 0.2 to 10 parts by weight of substituted phosphoric acid) to 100 parts by weight of polymeric solids.

When a latex primary adhesive prepared with an ammoniated phosphoric acid derivative is cured during carpet manufacture, the ammonia is expelled, leaving the biocidal phosphoric acid ester or its salt in the cured latex.

The biocidal tuftlock precoat or fusion bonding adhesive can be formulated with other compounds to increase its suitability as an adhesive and to impart added beneficial properties to the carpet. For example, a flame retardant can be added such as alumina trihydrate, which at high temperature generates steam instead of smoke. Other flame retardant compounds which can be used include inorganic carbonates, such as $CaCO_3$, $MgCO_3$, $BaCO_3$, metal oxides, borates, sulfonates, phosphates, and halogenated organic compounds such as pentabromophenyl ether.

A dispersing agent can be added to the formulation to insure that the flame retardant is sufficiently evenly distributed. An example is Narlex-LD 45 by National Starch and Chemical Corporation.

A defoamer can be added to increase the density of the adhesive on curing. An example of a defoaming agent is Foammaster VF from Henkel Corporation.

The viscosity of the adhesive or precoat can be adjusted as necessary with a thickener such as Natrosol 250HR by Hercules, Inc. or Paragum 141 by Parachem Southern, Inc. Natrosol 250 HR is activated at a pH of greater than 7.0. If necessary, a base such as ammonia can be added to the polymeric formulation to increase the pH when Natrosol is used.

Catalysts can be added to crosslink latex adhesives. For example, ammonium chloride acts as a catalyst to crosslink vinyl acetate ethylene copolymers. Crosslinking of a latex adhesive with the aid of compounds such as melamine is beneficial to prevent softening and degradation of the adhesive layer on exposure to water.

In general, a fusion bonding adhesive must have stronger adhering properties than a tuftlock precoat, because a fusion bonding adhesive bonds fibers to a base layer, whereas a precoat merely secures fibers which are woven or tufted through a primary backing. Fusion bonding adhesives, therefore, must have less filler and a higher relative proportion of polymer than tuftlock precoats.

Tables 1-7 below provide examples of formulations for tuftlock precoats and fusion bonding adhesives for antimicrobial carpet and carpet tile. The ingredients are expressed in parts by weight. Variations of these formulations can be prepared within the scope of this invention.

EXAMPLE 6

Antimicrobial Fusion Bonding Adhesive Prepared with a Latex Polymer

TABLE 1

| Ingredient | Parts By Weight |
| --- | --- |
| Latex | 180-250 |

TABLE 1-continued

| Ingredient | Parts By Weight |
|---|---|
| Alumina Tri-Hydrate | 50–250 |
| Ammonium Chloride | 0–10 |
| Ammonia | as required to raise pH above 7.0 if Natrosol 250 HR is used |
| Narlex-LD 45 (Dispersing Agent for ATH) | 0–3 |
| Defoamer | 0–3 |
| Natrosol 250HR (Thickener) | as required to acheive desired viscosity |
| Cymel 373 (Crosslinking Agent) | 0–10 |
| Ammoniated Phosphoric Acid Ester or its Salt | 0.3–13.50 |

EXAMPLE 7

Antimicrobial Fusion Bonding Adhesive Prepared with a Vinyl Acetate Ethylene Copolymer

TABLE 2

| Ingredient | Parts By Weight |
|---|---|
| VAE Latex | 192 |
| Aluminum Tri-Hydrate | 100 |
| Ammonium Chloride | 3.9 |
| DeFoamer | 0.1 |
| Ammonia | as needed to give pH of 7.5 |
| Natrosol 250 HR | as needed to achieve desired viscosity |
| Ammoniated Phosphoric Acid Ester or its Salt | 0.3–13.50 |

EXAMPLE 8

Antimicrobial Fusion Bonding Adhesive Prepared with a Styrene Butadiene Polymer

TABLE 3

| Ingredient | Parts By Weight |
|---|---|
| SBR latex | 200 |
| Alumina Trihydrate | 100 |
| defoamer | 0.1 |
| dispersant | 0.1 |
| Paragum 141 | as needed to acheive desired viscosity |
| Ammoniated Phosphoric Acid Ester or its Salt | 0.3–13.50 |

EXAMPLE 9

Antimicrobial Fusion Bonding Adhesive Prepared with a Vinyl Acetate Acrylate Ester Copolymer

TABLE 4

| Ingredient | Parts By Weight |
|---|---|
| Vinyl acetate acrylate ester | 217 |
| Alumina Trihydrate | 100 |
| defoamer | 0.1 |
| dispersant | 0.1 |
| Paragum 141 | as needed to achieve desired viscosity |
| Ammoniated Phosphoric Acid Ester or its Salt | 0.3–13.50 |

EXAMPLE 10

Antimicrobial Tuftlock Precoat Prepared with a Vinyl Acetate Ethylene Copolymer

TABLE 5

| Ingredient | Parts By Weight |
|---|---|
| VAE Latex | 192 |
| Alumina Trihydrate | 150 |
| Ammonia | as required to raise pH above 7.0 if Natrosol 250 HR is used |
| Narlex-LD 45 (Dispersing Agent for ATH) | 0–3 |
| Defoamer | 0–3 |
| Natrosol 250HR (Thickener) | as required to achieve required viscosity |
| Cymel 373 | 0–10 |
| Ammoniated Phosphoric Acid Ester or its Salt | 0.3–13.50 |

EXAMPLE 11

Antimicrobial Tuftlock Precoat Prepared with a Styrene Butadiene Polymer

TABLE 6

| Ingredient | Parts By Weight |
|---|---|
| SBR latex | 200 |
| Alumina Trihydrate | 150 |
| defoamer | 0.1 |
| dispersant | 0.1 |
| Paragum 141 | as needed to achieve desired viscosity |
| Ammoniated Phosphoric Acid Ester or its Salt | 0.3–13.50 |

EXAMPLE 12

Antimicrobial Tuftlock Precoat Prepared with a Vinyl Acetate Acrylate Ester Copolymer

TABLE 7

| Ingredient | Parts By Weight |
|---|---|
| Vinyl acetate acrylate ester | 217 |
| Alumina Trihydrate | 150 |
| defoamer | 0.1 |
| dispersant | 0.1 |
| Paragum 141 | as needed to achieve desired viscosity |
| Ammoniated Phosphoric Acid Ester or its Salt | 0.3–13.50 |

BIOCIDAL EFFECT OF ANTIMICROBIAL CARPET AND CARPET TILE

Carpet and carpet tile prepared according to the present invention is protected from microbial growth both at the primary backing and on the fibers, because the phosphoric acid ester migrates from the adhesive up the fibers over time. Further, the continuous migration of the phosphoric acid ester serves to replenish to biocide to the fibers, providing long term effectiveness.

Fusion bonded and tufted carpet prepared with biocidal vinyl acetate ethylene primary adhesives were tested for their ability to inhibit the growth of a Gram positive organism (*S. aureus*), a Gram negative organism (*P. aeruginosa*), and a fungal organism (*A. niger*).

The following procedure was used for both fusion bonded and tufted carpet. An 18 hour nutrient broth culture of *S. aureus* was adjusted with sterile nutrient broth to an absorbency of 0.044 at 600 nm, representing a concentration of approximately $10^9$ cells/mL. An 18 hour nutrient broth culture of *P. aeruginosa* was adjusted with sterile nutrient broth to an absorbency of 0.042 at 600 nm, also representing a concentration of approximately $10^9$ cells/mL.

One 200 mL aliquot of nutrient agar was inoculated with 2 mL of $10^6$ cells/mL nutrient broth of *S. aureus*, and a second 200 mL aliquot of nutrient agar was inoculated with 2 mL of $10^6$ nutrient broth of *P. aeruginosa*, to yield final concentrations of $10^4$ cells per mL in each solution. Potato dextrose agar was inoculated with 2 mL of *A. niger* in a saline suspension. The inoculated agars were swirled until mixed.

Test and control carpet samples were cut into $1'' \times 1\frac{1}{2}''$ pieces. Half of each piece was shaved to the backing/base layer. Each sample was placed in a separate $100 \times 15$ mm sterile petri dish.

Sufficient inoculated agar was poured onto the carpet samples in the sterile petri dishes to cover the shaved base layer of the carpet. Sterile agar was used to cover the control sample. Sterile tongs were used to manipulate the carpet pieces in order to force the air out of the pieces and to insure that each piece was completely saturated. The dishes were then covered and the agar left to solidify at room temperature.

The dishes were placed in a 20° C. incubator for approximately 48 hours. The samples were then visually inspected for zones of inhibition against Gram-positive and fungal organisms at the backing and fiber layers. A stereomicroscope was used to evaluate surface inhibition of Gram-negative bacteria.

EXAMPLE 13

Inhibition of Microbial Growth on Fusion Bonded Carpet Tile Prepared With a VAE Adhesive Fusion bonded I-tuft carpet tile was prepared with nylon fibers adhered to a fiberglass primary backing with a vinyl acetate ethylene biocidal adhesive prepared as in Example 7, with 3.5 parts by weight of ammoniated phosphoric acid ester as prepared in Example 4. A secondary backing of plasticized polyvinyl chloride was applied.

During the course of manufacture, the top layer of I-tufted carpet fusion bonded carpet is given two heat treatments while the bottom layer is given one heat treatment. In order to test the effect of additional cure on the biocidal effect of the carpet, the carpet samples were labeled "top" or "bottom", on the basis of whether they exited the carpet tile production line as the top or bottom layer of the I-tuft precursor carpet.

The results of Experiment One and Two are presented in Tables 8-9. Both "top" and "bottom" carpet samples exhibited good zones of inhibition against Gram positive and fungal organisms, and either a zone of inhibition or good surface inhibition against Gram negative organisms.

TABLE 8

| Tile Run | Experiment One | | | | | |
|---|---|---|---|---|---|---|
| | S. aureus | | P. aeruginosa | | A. niger | |
| Position | B | F | B | F | B | F |
| Top | − | − | − | − | − | − |
| Bottom | − | −* | − | − | − | ± (5 colonies) |
| Top | − | −* | − | − | − | ± (1 colony) |
| Bottom | − | − | − | − | ± | ± |

TABLE 8-continued

| Tile Run | Experiment One | | | | | |
|---|---|---|---|---|---|---|
| | S. aureus | | P. aeruginosa | | A. niger | |
| Position | B | F | B | F | B | F |
| Control | + | + | + | + | + | + |

+ "Growth" — no bacterial inhibition.
− No growth — good bacterial inhibition.
± Spotty inhibition with some colonies on carpet.
*These samples produced larger zones of inhibition against the Gram-positive bacteria.

TABLE 9

| Tile Run | Experiment Two | | | | | |
|---|---|---|---|---|---|---|
| | S. aureus | | P. aeruginosa | | A. niger | |
| Position | B | F | B | F | B | F |
| Top | − | − | + | + | − | − |
| Bottom | − | − | SI | SI | − | − |
| Top | − | − | SI | SI | − | − |
| Bottom | − | − | SI | SI | − | − |
| Control | + | + | + | + | + | + |

EXAMPLE 14

Inhibition of Microbial Growth on Tufted Carpet Tile Prepared With a VAE Adhesive Tufted carpet tile was prepared with nylon fibers tufted into a woven polypropylene primary backing and adhered with a vinyl acetate ethylene biocidal precoat prepared as in Example 10, with 0.5-3 parts per weight of VAE polymer solids of ammoniated phosphoric acid ester as prepared in Example 4.

In Experiment Three, one tufted sample was tested without a secondary backing, and a second sample was tested with a thick polyvinyl chloride plastisol secondary backing as used in carpet tile. The results of Experiment Three are presented in Table 10. Both the unbacked and the PVC backed carpet tile exhibited good zones of inhibition against Gram positive and fungal organisms. There was good surface inhibition of the Gram negative organism at the primary backing.

TABLE 10

| Tufted Carpet Sample | Experiment Three | | | | | |
|---|---|---|---|---|---|---|
| | S. aureus | | P. aeruginosa | | A. niger | |
| | B | F | B | F | B | F |
| No secondary backing | − | − | SI | + | − | − |
| PVC Plastisol secondary backing | − | − | SI | + | − | − |
| Control | + | + | + | + | + | + |

Key:
+ "Growth" — No inhibition
− "No Growth" — Good inhibition
SI Good surface inhibition (fewer colonies, but not zone of inhibition)

In Experiment Four, Quantum Plus II and Basics Plus carpet products, which are tufted loop pile nylon carpet tiles with VAE primary backings and plasticized PVC secondary backings, were tested for inhibition of Gram positive, Gram negative and fungal organisms. The results are presented in Table 11.

TABLE 11

| Carpet Sample Description | Experiment Four | | |
|---|---|---|---|
| | S. aureus | P. aeruginosa | A. niger |
| 3 Quantum Plus II Samples | − | SI | − |
| | | SI | |

TABLE 11-continued

| Carpet Sample Description | Experiment Four | | |
|---|---|---|---|
| | S. aureus | P. aeruginosa | A. niger |
| | — | SI | — |
| 1 Basics Plus Sample | — | SI | — |

As shown, all four samples exhibited a zone of inhibition against Gram positive and fungal organisms and good surface inhibition of Gram negative organisms.

In Experiment Five, two samples of tufted carpet with a vinyl acetate ethylene precoat, nylon fibers, and a plasticized polyvinyl chloride secondary backing were tested for their biocidal properties against Gram positive and Gram negative organisms, with AATCC Antibacterial Test Methods 100 and 147. Sample 1 had 1.1% of ammoniated di-(2-hydroxyethyl)cocoamine salt of 2-ethylhexylphosphoric acid in the precoat, and sample 2 had 1.5% of the same compound in the precoat. The results are provided in Tables 12 and 13. The results of both AATCC tests 147 and 100 indicate good performance of the carpet tile against Gram positive and Gram negative organisms.

TABLE 12

| | AATCC Method 100 | |
|---|---|---|
| | S. aureus | P. aeruginosa |
| 1 | 100% Reduction | 100% Reduction |
| 2 | 100% Reduction | 99.9% Reduction |
| | AATCC Method 100 | |
| | S. aureus | P. aeruginosa |
| 1 | 100% Reduction | 99.9% Reduction |
| 2 | 86% Reduction | 97.1% Reduction |

TABLE 13

| AATCC Method 147 (Shaved Backing in Contact with Acar) | | |
|---|---|---|
| | S. aureus | K. pneumonia |
| Control | 0 mm | 0 mm |
| 1 | 3-5 mm | 1-3 mm |
| 2 | 3-5 mm | 1-3 mm |

CARPET TILE WITH BIOCIDAL SECONDARY BACKING

Microorganisms can accumulate not only in carpet fibers and at the primary backing, but also between the floor and the secondary backing of carpet or carpet tile, causing a foul odor and creating an unsanitary condition.

In an additional embodiment of the present invention, a biocidally effective amount of the phosphoric acid ester is added to the secondary backing of carpet to impart resistance to microbiocidal growth between the carpet and the floor.

The phosphoric acid ester or its salt is added to the secondary backing in a range of 0.2-10 parts per 100 parts by weight of base material solids. If the base material is a water based system, and especially one with a pH of greater than 7.0, the phosphoric acid ester should be added in an ammoniated form. Any base material suitable as a secondary backing can be used, for example polyvinyl chloride, ethylene vinyl acetate, polycarbonate, styrene butadiene rubber, ethylene propylene dicyclopentadiene (EPDM or EPTR), neoprene (poly(1,4-chloroprene)), acrylonitrile copolymers, bitumen or urethane. Fillers and additives used in the art, including those described for use in the biocidal primary adhesive, can be added to the secondary backing along with the phosphoric acid ester. Table 14 provides an example of an antimicrobial secondary backing composition.

TABLE 14

| PVC Resin | 100 parts |
|---|---|
| Plasticizer (Dioctylphthalate) | 30-70 parts |
| CaCO₃ filler | 0-250 parts |
| Heat Stabilizer | 0-0.5 parts |
| Phosphoric Acid Ester or its salt | 0.2-10 parts |

Modifications and variations of the present invention, antimicrobial carpet and carpet tile and to method of preparing it, will be obvious to those skilled in the art from the foregoing description. Such modifications and variations are intended to come within the scope of the appended claims.

We claim:

1. An antimicrobial carpet comprising fibers attached to a primary backing with a primary adhesive that includes:
   (i) a biocidally effective amount of a phosphoric acid ester of the general formula:

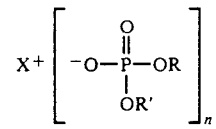

wherein R and R' are alkyl, oxyalkyl, polyoxyalkyl, aryl, aralkyl or alkaryl groups of $C_1$ to $C_{24}$, and one of R or R' can be H; X is a Group I metal ion, Group II metal ion, transition metal ion, or $NY_1Y_2Y_3Y_4$, where $Y_{1-4}$ are hydrogen, a hydrocarbon of $C_1$ to $C_{24}$, or a hydroxyalkyl group of $C_1$ to $C_{24}$; and there is at least one free hydroxyl group; and when X is $NY_1Y_2Y_3Y_4$ or a Group I metal ion, n is 1, when X is a Group II metal ion, n is 2; and when X is a transition metal, n is equal to the valence of the metal; and
   (ii) a latex polymer; and
   wherein the phosphoric acid ester or its salt is capable of migration from the primary adhesive to the fibers.

2. The carpet of claim 1 wherein the adhesive contains between approximately 0.2 and 10 parts by weight of the phosphoric acid ester to 100 parts by weight of polymeric solids.

3. The carpet of claim 2 wherein the adhesive contains between approximately 2.5 and 3.0 parts by weight of the phosphoric acid ester to 100 parts by weight of polymeric solids.

4. The carpet of claim 1 wherein the polymer is selected from the group consisting of polymers and copolymers of vinyl acetate-ethylene, styrene-butadiene, vinylidene chloride, vinyl chloride, cellulose acetate butyrate, vinyl chloride-acrylonitrile, vinyl acetate-acrylic acid, vinylidene chloride-acrylonitrile, acrylic acid-methacrylic acid, butadiene-acrylonitrile, acrylic acid-styrene, acrylonitrile-styrene, acrylonitrile-acrylic acid, acrylonitrile-alkyl acrylate, acrylonitrile butadiene styrene, and vinyl acetate acrylate ester.

5. The carpet of claim 4 wherein the polymer is vinyl acetate-ethylene.

6. The carpet of claim 5 wherein R is 2-ethylhexyl and R' is H.

7. The carpet of claim 6 wherein X+ is di-(2-hydroxyethyl)cocoamine.

8. The carpet of claim 1 comprising pile yarn and a primary backing, wherein the primary adhesive bonds the pile yarn to the primary backing.

9. The carpet of claim 1 comprising pile yarn and a primary backing, wherein the primary adhesive bonds yarn that is tufted through a primary backing.

10. The carpet of claim 1 comprising pile yarn and a primary backing, wherein the primary adhesive bonds yarn that is woven through a primary backing.

11. The carpet of claim 1, wherein the primary adhesive further comprises a compound selected from the group consisting of a flame retardant, a dispersing agent, a defoamer, a viscosity adjusting agent, a catalyst for crosslinking, and a filler.

12. The carpet of claim 11, wherein the flame retardant is alumina trihydrate.

13. An antimicrobial carpet with a secondary backing comprising a polymeric or bitumen base material that includes a biocidally effective amount of a phosphoric acid ester of the general formula:

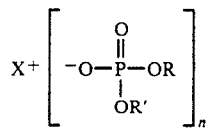

wherein R and R' are alkyl, oxyalkyl, polyoxyalkyl, aryl, aralkyl or alkaryl groups of $C_1$ to $C_{24}$, and one of R or R' can be H; X is a Group I metal ion, Group II metal ion, transition metal ion, or $NY_1Y_2Y_3Y_4$, where $Y_{1-4}$ are hydrogen, a hydrocarbon of $C_1$ to $C_{24}$, or a hydroxyalkyl group; of $C_1$ to $C_{24}$; and there is at least one free hydroxyl group; and when X is a Group I metal ion, n is 1, when X is a Group II metal ion, n is 2; and when X is a transition metal, n is equal to the valence of the metal.

14. The antimicrobial carpet of claim 13, wherein between approximately 0.2 and 10 parts of phosphoric acid ester are added to the secondary backing per 100 parts by weight of base material.

15. The antimicrobial carpet of claim 13, wherein the base material is selected from the group consisting of polyvinyl chloride, ethylene vinyl acetate, polycarbonate, styrene butadiene rubber, ethylene propylene dicyclopentadiene (EPDM or EPTR), neoprene (poly(1,4-chloroprene)), acrylonitrile copolymers, bitumen and urethane.

16. A method of preparing an antimicrobial carpet that includes fibers attached to a primary backing with a primary adhesive, comprising:
applying the primary adhesive to the primary backing, wherein the primary adhesive includes:

(i) a biocidally effective amount of a phosphoric acid ester of the general formula:

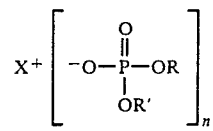

wherein R and R' are alkyl, oxyalkyl, polyoxyalkyl, aryl, aralkyl or alkaryl groups of $C_1$ to $C_{24}$, and one of R or R' can be H; X is a Group I metal ion, Group II metal ion, transition metal ion, or $NY_1Y_2Y_3Y_4$, where $Y_{1-4}$ are hydrogen, a hydrocarbon of $C_1$ to $C_{24}$, or a hydroxyalkyl group of $C_1$ to $C_{24}$; and there is at least one free hydroxyl group; and when X is a Group I metal ion, n is 1, when X is a Group II metal ion, n is 2; and when X is a transition metal, n is equal to the valence of the metal; and (ii) a latex polymer;
and wherein the phosphoric acid ester is capable of migrating from the primary adhesive to the carpet fibers.

17. The method of claim 16 further comprising adding between approximately 0.2 and 10 parts by weight of phosphoric acid ester per 100 parts by weight of polymer.

18. The method of claim 17 further comprising adding between approximately 2.5 and 3.0 parts by weight of phosphoric acid ester per 100 parts by weight of polymer.

19. The method of claim 16, further comprising preparing the primary adhesive by:
i) mixing the phosphoric acid ester with an aqueous solution of ammonia;
ii) adding the ammoniated phosphoric acid ester solution to a solution of the polymer.

20. The method of claim 19 further comprising selecting the polymer from the group consisting of polymers and copolymers of vinyl acetate-ethylene, styrene-butadiene, vinylidene chloride, vinyl chloride, cellulose acetate butyrate, vinyl chloride-acrylonitrile, vinyl acetate-acrylic acid, vinylidene chloride-acrylonitrile, acrylic acid-methacrylic acid, butadiene-acrylonitrile, acrylic acid-styrene, acrylonitrile-styrene, acrylonitrile-acrylic acid, acrylonitrile-alkyl acrylate, acrylonitrile butadiene styrene, and vinyl acetate acrylic ester.

21. The method of claim 20 further comprising adding between approximately 0.3 and 13.50 parts by weight of ammoniated phosphoric acid ester to 100 parts by weight of the polymer in solution.

22. The method of claim 20 further comprising adding a compound selected from the group consisting of a flame retardant, a dispersing agent, a defoamer, a viscosity adjusting agent, a catalyst for crosslinking, and a filler.

* * * * *

UNITED STATES PATENT AND TRADEMARK OFFICE
CERTIFICATE OF CORRECTION

PATENT NO. : 5,024,840

DATED : June 18, 1991

INVENTOR(S) : Lawrence W. Blakely, Michael A. Howe, Daniel F. Pinholster, Jr., Claude E. Terry, Robert H. McIntosh, Sr.

It is certified that error appears in the above-identified patent and that said Letters Patent is hereby corrected as shown below:

Column 5, line 23: Replace "n" with "no".

Column 15, line 37: Replace "or a hydroxyalkyl group; of $C_1$ to $C_{24}$;" with "or a hydroxyalky group of $C_1$ to $C_{24}$;"

Abstract, line 3: Replace "non-plasticized PVC" with "non-PVC".

Signed and Sealed this

Twenty-sixth Day of January, 1993

Attest:

STEPHEN G. KUNIN

Attesting Officer

Acting Commissioner of Patents and Trademarks